United States Patent
Stakutis et al.

(10) Patent No.: US 8,655,320 B2
(45) Date of Patent: Feb. 18, 2014

(54) METHOD AND SYSTEM FOR PROVIDING LOW-COMPLEXITY VOICE MESSAGING

(75) Inventors: Christopher J. Stakutis, Concord, MA (US); Thomas M. Boyle, Norfolk, MA (US); Steven L. Greenspan, Scotch Plains, NJ (US)

(73) Assignee: CA, Inc., Islandia, NY (US)

( * ) Notice: Subject to any disclaimer, the term of this patent is extended or adjusted under 35 U.S.C. 154(b) by 779 days.

(21) Appl. No.: 12/423,231

(22) Filed: Apr. 14, 2009

(65) Prior Publication Data

US 2010/0261456 A1  Oct. 14, 2010

(51) Int. Cl.
*H04L 12/58* (2006.01)
*H04M 1/725* (2006.01)

(52) U.S. Cl.
USPC ............. 455/412.1; 455/412.2; 455/466; 455/564; 704/207; 704/208; 704/214; 704/246

(58) Field of Classification Search
USPC .............. 455/412, 412.2, 466, 564; 704/207, 704/208, 214, 246
See application file for complete search history.

(56) References Cited

U.S. PATENT DOCUMENTS

| | | | | |
|---|---|---|---|---|
| 5,666,350 | A * | 9/1997 | Huang et al. | 370/435 |
| 2002/0034956 | A1* | 3/2002 | Mekuria | 455/466 |
| 2002/0121981 | A1* | 9/2002 | Munch | 340/576 |
| 2004/0109571 | A1* | 6/2004 | Yoshimine | 381/67 |
| 2005/0266863 | A1* | 12/2005 | Benco et al. | 455/466 |
| 2007/0021687 | A1* | 1/2007 | Keith et al. | 600/587 |
| 2008/0089503 | A1* | 4/2008 | Crockett et al. | 379/201.03 |
| 2008/0212746 | A1* | 9/2008 | Gupta et al. | 379/38 |

OTHER PUBLICATIONS

Chumby Industries, "About Chumby," http://www.chumby.com/pages/media_factsheet, Copyright 2006-2009, 3 pages.

* cited by examiner

*Primary Examiner* — Liton Miah
(74) *Attorney, Agent, or Firm* — Baker Botts, LLP

(57) ABSTRACT

A voice messaging system includes a transceiver, an indicator, a microphone, and a speaker. The transceiver is operable to receive a message from the Internet, and the indicator is operable to announce that the message has been received. The microphone is operable to receive a verbal request to play the message, and the speaker is operable to play the recorded message in response to receiving the verbal request.

17 Claims, 2 Drawing Sheets

METHOD AND SYSTEM FOR PROVIDING LOW-COMPLEXITY VOICE MESSAGING

TECHNICAL FIELD

This disclosure relates generally to the field of electronics and more specifically to a method and system for providing low-complexity voice messaging.

BACKGROUND

Voice messaging devices such as telephones, cell phones, and computers are prevalent in today's society. Such devices enable a user to send and receive voice messages to other users. In certain situations, typical voice messaging devices may not be practical for users who have special needs.

SUMMARY OF THE DISCLOSURE

According to one embodiment of the present disclosure, a voice messaging system includes a transceiver, an indicator, a microphone, and a speaker. The transceiver is operable to receive a message from the Internet, and the indicator is operable to announce that the message has been received. The microphone is operable to receive a verbal request to play the message, and the speaker is operable to play the recorded message in response to receiving the verbal request.

Certain embodiments of the disclosure may provide one or more technical advantages. A technical advantage of one embodiment may be that a user can send and receive voice messages with little or no physical interaction with the system. A technical advantage of another embodiment may be that the system may analyze the voice of a user and provide a medical diagnosis.

Certain embodiments of the disclosure may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION OF THE DRAWINGS

Figure 1:
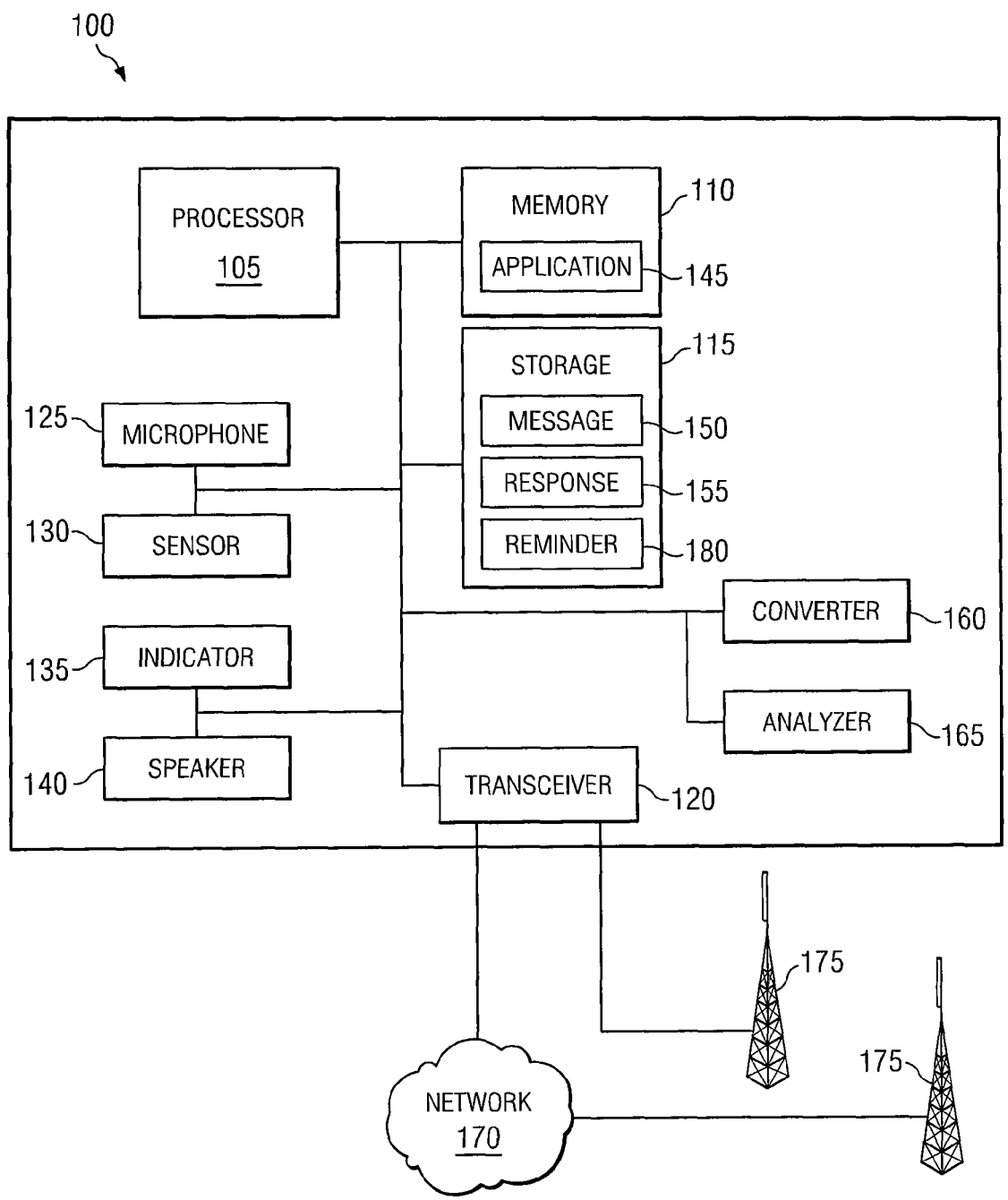
FIG. 1 is a block diagram illustrating a system that may be utilized to provide voice messaging.
Figure 2:
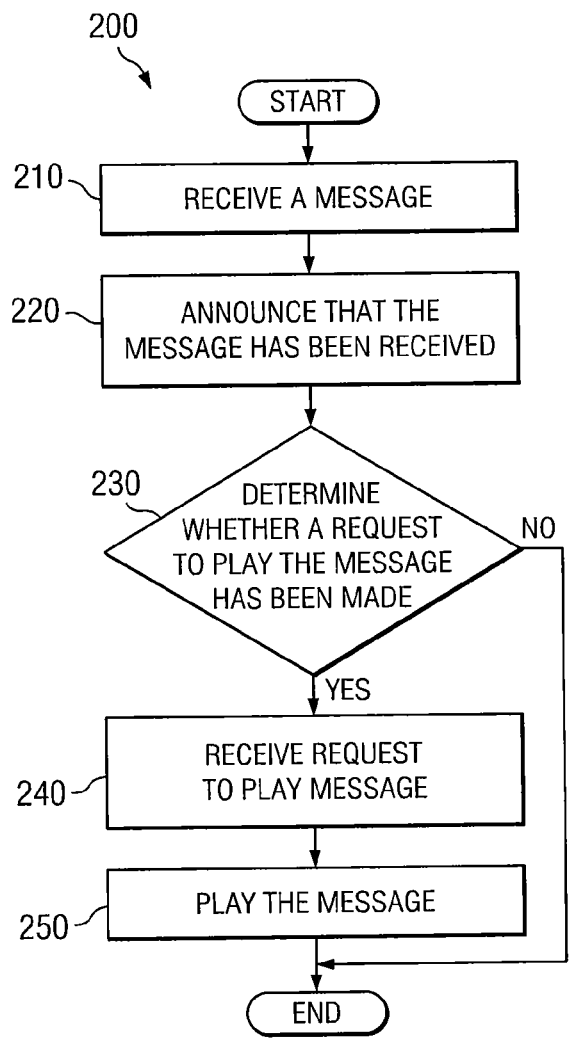
FIG. 2 is a flowchart illustrating a voice messaging method in accordance with a particular embodiment of this disclosure.
Figure 3:
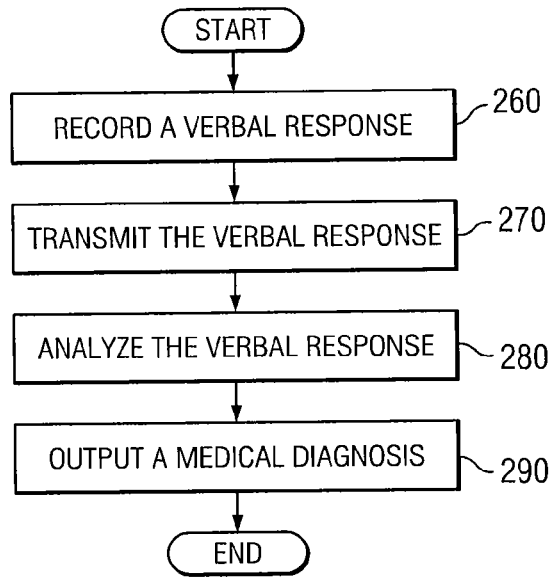
FIG. 3 is a flow chart illustrating another voice messaging method in accordance with a particular embodiment of this disclosure.

Embodiments of the present disclosure and its advantages are best understood by referring to FIGS. 1 through 3 of the drawings, like numerals being used for like and corresponding parts of the various drawings.

Many elderly and chronically ill patients are home-bound or otherwise isolated from other people. They may go for days without speaking to another person, for example, until a nurse visits or the patient goes to a store. The patients may be able to check email and make phone calls, but such tasks typically require more effort than watching TV or listening to the radio. The sound of a loved one's or caregiver's voice may offer comfort and spontaneity for a patient during these times. In addition, the sound of a patient's voice may offer insight into the patient's health that is not provided by an email or text message.

Known "connected health" or "telemedicine" devices are generally complicated to use and might not provide adequate voice contact. These devices typically require an amount of interaction and technological savvy that may discourage most elderly and chronically ill patients from using them. As a result, these devices may fail to provide an easy way to attain the routine human-to-human voice contact needed to maintain good health.

The teachings of the disclosure recognize that it would be desirable to provide human-to-human voice and/or video based messaging with low complexity and high spontaneity. FIGS. 1 through 3 below illustrate a system and method of providing voice messaging according to the teachings of the disclosure.

FIG. 1 illustrates an embodiment of a system 100 that may be used to provide voice messaging to a user with minimal or no physical interaction with the system. For example, system 100 may deliver and receive voice messages in response to a verbal request from a user.

In the illustrated embodiment, system 100 includes a processor 105, a memory device 110, a storage device 115, a transceiver 120, a microphone 125, a sensor 130, an indicator 135, a speaker 140, a converter 160, and an analyzer 165. Memory device 110 stores an application 145, and storage device 115 stores a message 150, a verbal response 155, and a reminder 180. System 100 may be coupled to a network 170 using a wired connection or a wireless connection via one or more wireless devices 175. The components 105-165 of system 100 may be coupled to each other in any suitable manner, such as by a bus or via other components not specifically shown in FIG. 1.

In operation, system 100 provides voice messaging to a user based on minimal or no physical interaction with the system. For example, system 100 may receive message 150 from network 170 via transceiver 120. System 100 may indicate to a user via indicator 135 that message 150 is available and then play received message 150 via speaker 140. System 100 may then receive response 155 from the user via microphone 125 and transmit response 155 to network 170. In certain embodiments, system 100 may analyze response 155 via analyzer 165 in order to determine a medical diagnosis.

Processor 105 generally refers to any suitable processing device capable of executing instructions and manipulating data to perform operations for system 100. For example, processor 105 may include any type of multi-core central processing unit (CPU). Functions that processor 105 may perform include voice messaging operations as described below.

Memory device 110 may refer to any suitable device capable of storing and facilitating retrieval of data. Examples of memory device 110 include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable medium. In this example, application 145 embodied as logic within memory device 110 generally provides voice messaging operations as described below. Alternatively, application 145 may reside within any of a variety of other suitable computer-readable medium, including, for example, storage device 115.

Transceiver 120 may refer to any suitable device capable of receiving input for system 100, sending output from system 100, performing suitable processing of the input or output or both, communicating to other devices, or any combination of the preceding. For example, transceiver 120 may include appropriate hardware (e.g., modem, network interface card, etc.) and/or software (e.g., protocol conversion and data processing software) to communicate through a local area network (LAN), a metropolitan area network (MAN), a wide-area network (WAN), or other communication network that allows system 100 to communicate to other devices. Transceiver 120 may include one or more ports, conversion software, or both. Transceiver 120 may be coupled to network 170 and/or wireless device 175.

Storage device 115 may refer to any suitable device capable of storing computer-readable data and instructions. Storage device 115 may be similar to memory device 110 as described above.

Microphone 125 may be any type of microphone device that is capable of receiving and transmitting sound, such as a voice. Microphone 125 may be physically integrated into system 100 or may be a separate device that is coupled to system 100. For example, a separate microphone 125 may be coupled to system 100 via a Universal Serial Bus (USB) connection.

Sensor 130 may be any type of sensor device that is capable of receiving a physical input from a user. As an example, sensor 130 may be a movement sensor that detects whether a user has shaken or touched system 100 in order to play message 150. As another example, sensor 130 may be a simple button or a touch screen. As yet another example, sensor 130 may be a proximity sensor that senses when a user is within a predetermined distance of system 100. In such an example, system 100 may continuously announce that a message is available when a user is within the predetermined distance of system 100.

Indicator 135 may refer to any suitable device capable of alerting a user. For example, indicator 135 may be any type of visual indicator, movement indicator, or audible indicator. Example visual indicators include lights, liquid crystal display (LCD) screens, light emitting diodes (LEDs), or any other type of indicator that may alert a user who is not visually impaired. Example movement indicators include a vibration device or any other device that may alert a user via movement. Example audible indicators include a speaker such as speaker 140 or any other device that may alert a user who is not audibly impaired.

Speaker 140 may be any type of type of speaker that is capable of audibly playing a message to a user. Certain embodiments may include more than one speaker 140.

Converter 160 may be any device that is capable of converting text to speech and/or vice versa. In certain embodiments, converter 160 may be logic in the form of a software application that resides in memory device 110 and/or storage device 115.

Analyzer 165 may be any device that is capable of analyzing sound. In particular embodiments, analyzer 165 may be logic in the form of a software application that resides in memory device 110 and/or storage device 115.

The components of system 100 may be integrated or separated. In some embodiments, components 105-165 may each be housed within a single chassis. The operations of system 100 may be performed by more, fewer, or other components. Additionally, operations of system 100 may be performed using any suitable logic that may comprise software, hardware, other logic, or any suitable combination of the preceding.

In general, network 170 may include at least a portion of a public switched telephone network (PSTN), a public or private data network, a LAN, a MAN, a WAN, a local, regional, or global communication or computer network such as the Internet, a wireline or wireless network, an enterprise intranet, other suitable communication link, or any combination of the preceding.

FIG. 2 illustrates an embodiment of a method 200 that may be used to provide voice messaging to a user based on minimal or no physical interactions. For example, method 200 may be application 145 as described above with reference to FIG. 1.

Method 200 begins in step 210 where a message is received. For example, message 150 may be received from network 170 via transceiver 120. Message 150 may be a message of any form including, but not limited to, a voice message, a video message, a text message, or an email message. In certain embodiments, message 150 may be stored in storage device 115 and/or memory device 110.

Once message 150 has been received, method 200 announces in step 220 that message 150 is available. For example, speaker 140 may announce, "You have a new message from Chris—would you like to hear it now?" In other embodiments, indicator 135 may indicate message 150 is available.

In step 230, method 200 waits for and determines whether a request has been made to play the received message 150. The request may be received through any suitable component, such as microphone 125 or sensor 130. In certain embodiments, microphone 125 may listen for a user to make a verbal request to play message 150. For example, method 200 may listen for a user to say "yes" or "no" in response to the announcement "You have a new message from Chris —would you like to hear it now?" In such an embodiment, method 200 may be able to respond to any of a number of words such as "no", "yes", "yeah", "yup", and "later." In other embodiments, microphone 125 may additionally or alternatively listen for a user to make an unsolicited request to play message 150. For example, microphone 125 may passively listen for a user to make an unsolicited request such as "play all messages."

In certain embodiments, sensor 130 may additionally or alternatively sense a request to play message 150. For example, sensor 130 may sense whether a user has shaken, touched, or moved within a predetermined distance of system 100.

If method 200 determines in step 230 that a request to play message 150 has been made, method 200 proceeds to step 240 below. If method 200 determines in step 230 that a request to play message 150 has not been made, method 200 ends.

In step 240, method 200 receives the request to play the received message 150. Method 200 then plays message 150 in step 250. Any suitable component may play message 150, such as speaker 140. In certain embodiments, speaker 140 plays message 150. In other embodiments, however, a video screen plays a video message 150.

In particular embodiments, method 200 may first convert message 150 to an audible message that can be played via speaker 140. For example, if message 150 received from network 170 is a text message, email message, or any other non-audible message, method 200 may convert message 150 to an audible message with converter 160. After playing message 150, method 200 ends.

FIG. 3 illustrates another embodiment of method 200 that may be used to provide voice messaging to a user based on minimal physical interaction. In step 260, method 200 may listen for and record a verbal response 155 from a user via microphone 125. In particular embodiments, verbal response 155 may be made in response to message 150. For example, message 150 may be a message from a doctor such as "How are you doing today?" Method 200 may ask the user, "Would you like to respond?" In response, a user may make a verbal response 155 such as "I am not feeling well." Method 200 may record verbal response 155 in storage device 115 and/or memory 100.

In step 270, transceiver 120 transmits the verbal response 155 to network 170. For example, transceiver 120 may transmit verbal response 155 through the Internet to a physician for analysis. In particular embodiments, verbal response 155 may be converted to text via converter 160 prior to transmission to network 170.

In certain embodiments, method 200 may in step 280 analyze the verbal response 155 that was recorded in step 260. For example, analyzer 165 may analyze verbal response 155 to determine if the user's voice appears normal or has changed since a prior verbal response. In such embodiments, analyzer 165 may determine stress levels in verbal response 155 and expedite transmission and/or processing of verbal response 155. Additionally or alternatively, analyzer 165 may analyze verbal response 155 to determine a medical diagnosis. In step 290, method 200 may transmit the medical diagnosis to network 170 via transceiver 120.

Some embodiments of method 200 may provide other features while requiring minimal or no physical interaction from a user. For example, certain embodiments of method 200 may include a reminder 180 to be played to a user. Reminder 180 may be an audible message such as "take your medication" or "feed the dog" that speaker 140 plays based on a predetermined schedule. Reminder 180 may be, for example, stored in storage device 115 and/or memory 110 or received from network 170. In other embodiments, sensor 130 may include a proximity sensor to sense when a user is nearby. Upon sensing that a user is nearby, system 100 may repeatedly play reminder 180 or message 150 that has been received.

Although the embodiments in the disclosure have been described in detail, numerous changes, substitutions, variations, alterations, and modifications may be ascertained by those skilled in the art. For example, FIG. 1 includes speaker 140 that is operable to play a received message. Other embodiments, however, may include a video screen that displays a received message. In addition, while the methods and applications disclosed herein have been described with reference to system 100, certain embodiments may utilize more than one computing system to execute and/or run the disclosed methods and applications. It is intended that the present disclosure encompass all such changes, substitutions, variations, alterations, and modifications as falling within the spirit and scope of the appended claims.

What is claimed is:

1. A voice messaging system comprising:
a processor operable to perform one or more operations of the system;
a transceiver coupled to the processor and operable to receive a message from a network;
an indicator coupled to the processor and operable to announce that the message has been received;
a microphone coupled to the processor and operable to:
receive a verbal request from a user to play the message;
receive a verbal response to the message from the user;
a voice analyzer coupled to the processor and operable to compare the verbal response to a prior verbal response and output an indication of the result of the comparison;
a speaker coupled to the processor and operable to play the message in response to receiving the verbal request; and
wherein the transceiver is operable to transmit the verbal response in an expedited manner based on the indication of the result of the comparison.

2. The voice messaging system of claim 1, the indicator selected from a group consisting of a visual indicator, a movement indicator, and an audible indicator.

3. The voice messaging system of claim 1, the processor further operable to send the verbal response from the user to the network.

4. The voice messaging system of claim 1,
the message comprising a text message; and
the voice messaging system further comprising a converter operable to convert the text message into a voice message.

5. The voice messaging system of claim 1, further comprising a converter operable to convert the verbal response from the user into a text message.

6. The voice messaging system of claim 1, further comprising a sensor operable to receive a physical input as a request to play the message.

7. A voice messaging method comprising:
processing, by a processor, one or more operations of the system;
receiving, by a transceiver coupled to the processor, a message from a network;
announcing, using an indicator coupled to the processor, that the message has been received;
receiving, using a microphone coupled to the processor, a verbal request from a user to play the message;
receiving, using the microphone coupled to the processor, a verbal response to the message from the user;
playing, using a speaker coupled to the processor, the message in response to receiving the verbal request;
comparing the verbal response to a prior verbal response;
outputting an indication of the result of the comparison; and
transmitting, using the transceiver coupled to the processor, the verbal response in an expedited manner based on the indication of the result of the comparison.

8. The voice messaging method of claim 7, the indicator selected from a group consisting of a visual indicator, a movement indicator, and an audible indicator.

9. The voice messaging method of claim 7, further comprising sending the verbal response from the user to the network.

10. The voice messaging method of claim 7,
the message comprising a text message; and
the voice messaging method further comprising converting, using a converter, the text message into a voice message.

11. The voice messaging method of claim 7, further comprising converting, using a converter, the verbal response from the user into a text message.

12. The voice messaging method of claim 7, further comprising receiving, using a sensor, a physical input as a request to play the message.

13. One or more non-transitory computer-readable media encoded with computer executable code operable to:
process, by a processor, one or more operations of the system;
receive, by a transceiver coupled to the processor, a message from a network;
announce, using an indicator coupled to the processor, that the message has been received;
receive, using a microphone coupled to the processor, from a user a verbal request to play the message;

receive, using the microphone coupled to the processor, a verbal response to the message from the user;

play, using a speaker coupled to the processor, the message in response to receiving the verbal request;

compare, using a voice analyzer coupled to the processor, the verbal response to a prior verbal response;

output, using the voice analyzer coupled to the processor, an indication of the result of the comparison; and transmit, using the transceiver coupled to the processor, the verbal response in an expedited manner based on the indication of the result of the comparison.

14. The non-transitory computer-readable media of claim 13, the indicator selected from a group consisting of a visual indicator, a movement indicator, and an audible indicator.

15. The non-transitory computer-readable media of claim 13, further operable to send the verbal response from the user to the network.

16. The non-transitory computer-readable media of claim 13, the message comprising a text message; and the computer-readable media further operable to convert, using a converter, the text message into a voice message.

17. The non-transitory computer-readable media of claim 13, further operable to receive, using a sensor, a physical input as a request to play the message.

\* \* \* \* \*